US009999601B2

(12) United States Patent
McLellan et al.

(10) Patent No.: US 9,999,601 B2
(45) Date of Patent: *Jun. 19, 2018

(54) COMPOSITION AND METHOD FOR INHIBITION OF NERVE TRANSMISSION

(75) Inventors: Alexander McLellan, Halifax (CA); Frank Greenway, Baton Rouge, LA (US)

(73) Assignee: NEUROQUEST INC. (CA)

( * ) Notice: Subject to any disclaimer, the term of this patent is extended or adjusted under 35 U.S.C. 154(b) by 0 days. days.

This patent is subject to a terminal disclaimer.

(21) Appl. No.: 12/537,095

(22) Filed: Aug. 6, 2009

(65) Prior Publication Data
US 2011/0257255 A1   Oct. 20, 2011

Related U.S. Application Data

(63) Continuation of application No. PCT/CA2008/000236, filed on Feb. 6, 2008.

(60) Provisional application No. 60/899,642, filed on Feb. 6, 2007.

(51) Int. Cl.
| | |
|---|---|
| *A61K 31/45* | (2006.01) |
| *A61K 31/121* | (2006.01) |
| *A61K 31/122* | (2006.01) |
| *A61K 31/22* | (2006.01) |
| *A61K 31/351* | (2006.01) |
| *A61K 31/045* | (2006.01) |

(52) U.S. Cl.
CPC .......... *A61K 31/045* (2013.01); *A61K 31/121* (2013.01); *A61K 31/122* (2013.01); *A61K 31/22* (2013.01); *A61K 31/351* (2013.01)

(58) Field of Classification Search
CPC .. A61K 31/045; A61K 31/121; A61K 31/122; A61K 31/22; A61K 31/351
See application file for complete search history.

(56) References Cited

U.S. PATENT DOCUMENTS

| | | | |
|---|---|---|---|
| 4,311,617 A | 1/1982 | Ansari | |
| 4,579,677 A | 4/1986 | Hooper | |
| 4,826,875 A | 5/1989 | Chiesi | |
| 4,923,685 A | 5/1990 | Wuelknitz | |
| 4,940,583 A | 7/1990 | Thompson | |
| 5,260,313 A | 11/1993 | Frame | |
| 5,770,738 A | 6/1998 | Banholzer et al. | |
| 6,248,307 B1 | 6/2001 | Bomerman et al. | |
| 2003/0092636 A1 | 5/2003 | Silberstein | |
| 2003/0224072 A1 | 12/2003 | Frome | |
| 2005/0090557 A1 | 4/2005 | Muhammad et al. | |
| 2005/0112183 A1 | 5/2005 | Galer | |
| 2006/0004050 A1 | 1/2006 | Speicher et al. | |
| 2006/0222690 A1 | 10/2006 | Bley | |
| 2010/0099772 A1* | 4/2010 | Bean | A61K 31/085 514/626 |
| 2011/0014419 A1 | 1/2011 | McLellan | |
| 2013/0267571 A1 | 10/2013 | Reed | |
| 2014/0357725 A1 | 12/2014 | Weaver | |

FOREIGN PATENT DOCUMENTS

| | | |
|---|---|---|
| EP | 08 71 4559 | 1/2010 |
| WO | 93/17695 A1 | 9/1993 |
| WO | 2002/053151 | 7/2002 |
| WO | WO2003/049726 A1 | 6/2003 |
| WO | 2006014788 | 2/2006 |
| WO | 2007/095631 A2 | 8/2007 |
| WO | WO 2008/063603 A2 | 5/2008 |
| WO | 2008095297 A1 | 8/2008 |
| WO | 2008/108825 A2 | 9/2008 |
| WO | 2010/017626 | 2/2010 |
| WO | 2010/057295 A9 | 5/2010 |
| WO | 2012/034232 | 3/2012 |
| WO | 2013/008093 | 1/2013 |

OTHER PUBLICATIONS

Chawla et al., "Challenges in Polymorphism of Pharmaceuticals," CRIPS, Jan.-Mar. 2004, vol. 5, No. 1, pp. 9-12.*
Newman et al., "Solid-state analysis of the active pharmaceutical ingredient in drug products," DDT, Oct. 2003, vol. 8, No. 9, pp. 898-905.*
Shellie et al. "Comprehensive two-dimensional gas chromatography-mass spectrometry analysis of Pelagornium graveolens essential oil using rapid scanning quadropole mass spectrometry," Analyst, 2003, 128, pp. 879-883.*
Levitt et al. "Regulation of neocortical interneuron development and the implications for neurodevelopment disorders," Trends in Neurosciences, vol. 27, No. 7, Jul. 2004, pp. 400-406.*

(Continued)

*Primary Examiner* — Sreeni Padmanabhan
*Assistant Examiner* — Jody Karol
(74) *Attorney, Agent, or Firm* — Barnes & Thornburg LLP

(57) ABSTRACT

The presently claimed and disclosed invention(s) provides a therapeutically effective composition and method of inhibiting nerve cell transmission. In a preferred embodiment of the presently claimed and disclosed invention(s), the treatment of neuropathic pain utilizing terpene compounds isolated from plant essential oils or manufactured synthetically is detailed. These compounds, such as geraniol and citronellol, as well as chemical analogs thereof, used in combination or individually, can be used alone or in a composition with a pharmaceutically acceptable carrier in a suitable dosage form.

6 Claims, 3 Drawing Sheets

(56) References Cited

OTHER PUBLICATIONS

Peana et al., "Involvement of adenosine A1 and A2A receptors in (−)-linalool-induced antinocieption," Life Sciences, 78 (2006) 2471-2474.*
"Rose geranium essential oil information" [Online] http://www.essentialoils.co.za/essential-oils/rose-geranium.htm; retrieved Jan. 20, 2010, pp. 1-8.
"Bergamot essential oil information" [Online] http://www.essentialoils.co.za/essential-oils/bergamot.htm; retrieved on Jan. 20, 2010, pp. 1-8.
"Lavendar essential oil information" [Online] http://www.essentialoils.co.za/essential-oils/lavender.htm; retrieved Jan. 20, 2010, pp. 1-8.
Golshani Samira et al: "Antinociceptive effects of the essential oil of Dracocephalum kotschyi in the mouse writhing test"; Journal of Pharmacy & Pharmaceutical Sciences: A Publication of the Canadian Society for Pharmaceutical Sciences, Société Canadienne Des Sciences Pharmaceuitiques; Apr. 20, 2004, vol. 7, No. 1, pp. 76-79, XP002564434.
Alessandra T. Peana et al., "(−) Linalool produces antinociception in two experimental models of pain", European journal of pharmacology, vol. 460, No. 1, Jan. 1, 2003 (Jan. 1, 2003), pp. 37-41, XP055172891, ISSN: 0014-2999, DOI: 10.1016/50014-2999(02)02856-X.
Silva-Santos, A. et al., "Analysis of uses of essential oils and terpenics/terpenoids compounds by pharmaceutical industry through USPTO granted patents", Rev. Bras. Pl. Med. 2008, vol. 10, No. 1, pp. 8-15.
Abena et al., "Comparative Chemical and Analgesic Properties of Essential Oils of Cymonpogon Nardus (L) Rendle of Benin and Congo", African Journal of Traditional, AJTCAM/African Networks on Ethnomedicines 2007, vol. 4, No. 3, pp. 267-272.
Ortiz, Mario et al., "The combination of naproxen and citral reduces nociception and gastric damage in rats", Archives of Pharmacal Research, vol. 33, No. 10, Oct. 2010, pp. 1691-1697.
Stotz, Stephanie et al., "Citral Sensing by TRANSient Receptor Potential Channels in Dorsal Root Ganglion Neurons", Plos One, Public Library of Science, US, vol. 3, No. 5, May 7, 2008.
Gunthorpe, M et al., "Clinical development of TRPV1 antagonists: targeting a pivotal point in the pain pathway", Drug Discovery Today, vol. 14, No. 1-2, Jan. 1, 2009, pp. 56-67.WO2007095631.
Ghelardini, C. et al., "Local Anaesthetic Activity of Monoterpene and Phenylpropoanes of Essential Oils", Planta Med., vol. 67, p. 564-566, 2001.
Woolf et al., "Neuropathic pain: aetilogy, symptoms, mechanisms, and management", Lancet 1999; 353; 1959-64.
Zhang et al., "The Balance Between Excitation and Inhibition and Functional Sensory Processing in the Somatosensory Cortex", International Review of Neurobiology, 2011, vol. 97, DOI:10.1016/B978-0-12-385198-7.00012-6, pp. 305-333.
Brown et al., "Abnormalities of the balance between inhibition and excitation in the motor cortex of patients with cortical myoclonus", Brain (1996), 119, 309-317.
Moriera et al., "Effects of terpineol on the compound action potential of the rat sciatic nerve", Brazilian Journal of Medicine and Biological Research (2001) 34:1337-1340.
Ippolito et al., "Tyrosine Phosphorylation of Kir3.1 in Spinal Cord is Induced by Acute Inflammation, Chronic Neuropathic Pain, and Behavioral Stress", J. Biol. Chem. 2005, 280:41683-41693, Oct. 13, 2005.
Beekwilder et al/. "Kv1.1 Channels of Dorsal Root Ganglion Neurons Are Inhibited by n-Butyl-p-aminobenzoate, a Promising Anesthetic for the Treatment of Chronic Pain", The Journal of Pharmacology and Experimental Therapeutics, vol. 304, No. 2, pp. 531-538, 2003.
Cooper et al., "Ion channel genes and human neurological disease: Recent progress, prospects, and challenges", Proc. Natl. Acad. Sci. vol. 96, pp. 4759-4766, Apr. 1999.

Devor, Marshall, "Sodium Channels and Mechanisms of Neuropathic Pain", The Journal of Pain, vol. 7, No. 15 (January), Supplement 1, 2006: pp. S3-S12.
Olsen et al., "Progress in Epilepsy Research GABA and Epieptogenesis", Epilepsia, 38(4):399-407, 1997.
Cobos et al., "Mice lacking Dix1 show subtype-specific loss of interneurons, reduced inhibition and epilepsy", Nature Neuroscience vol. 8, No. 8, Aug. 2005.
Laumonnier et al., "X-Limnked Mental Retardation and Autism are Associated with a Mutation in the NLGN4 Gene, a Member of the Neuroligin Family", Am. J. Hum. Genet. 74:552-557, 2004.
Dani et al., "Reduced cortical activity due to a shift in the balance between excitation and inhibition in a mouse model of Rett Syndrome", 12560-12565, PNAS, Aug. 30, 2005, vol. 102, No. 35.
Nickell et al., "Evidence for GABAB-mediated inhibition of Transmission from the olfactory nerve to mitral cells in the rat olfactory bulb", Brain Res Bull., 1994:35(2); 119-23.
Cates et al., "2,2'-Phthaloyl-, 2,2'-isophthaloyl-, and 2,2'-terephthaloylbis{1,1,1-trimethylhydrazinium] dihydroxide, bis(inner salts); synthesis, partition coefficients, toxicity and effect on ganglionic transmission", J Pharm Sci. Apr. 1986;75(4)"407-9.
Excerpt from Mechanisms and Mediators of Neuropathic Pain, 2002 (textbook).
Pommer et al., "Industrial synthesis of terpene compounds", Pure and Applied Chemistry 43.3-4 (1975): 527-551.
Solis et al., "Antibacterial and Antifungal Terpenes from Pilgerodendron uviferum (D.DON) Florin", J. Chil. Chem. Soc. V.49 n.2 Concepcion Jun. 2004.
Taylor et al., "Pharmacology and mechanism of action of pregabalin: The calcium channel ɑ-2- δ (alpha2-delta) subunit as a target for antiepileptic drug discovery", Epilepsy Research (2007) 73, 137-150.
Zesiewicz et al., "A pilot, double-blind, placebo-controlled trial of pregabalin (Lyrica) in the treatment of essential tremor"; Movement Disorder 22.11 (2007): 1660-1663. (Abstract only).
Rose et al., Gabapentin: pharmacology and its use in pain management:, Anesthesia, 2002, 57, pp. 451-462.
Gironelli et al., "A Randomized Placebo-Controlled Comparative Trial of Gabapentin and Propranolo in Essential Tremor", Arch Neurol. 1999; 456:475-480.
Spina et al., "Antiepileptic drugs: indications other than epilepsy", Epileptic Disorders: international Epilepsy Journal with videotape 6.2 (2004):57-75. (Abstract only).
Merren, Gabapentin for treatment of pain and tremor: a large case series: Southern Medical Journal 91.8 (1998) 739-744. (Abstract only).
Porter, Pure Appl Chem, (1969),20: 449-481.
Kingery, Wade S_"A critical review of controlled clinical trials for peripheral neuropathic pain and complex regional pain syndromes." Pain 732 (1997): 123-139.
Kvarnstrom, Ann, et al. "The effectiveness of intravenous ketamine and lidocaine on peripheral neuropathic pain." Acta anaesthesiologica scandinavica47_7(2003): 868-877.
McCleane, Gary "Topical application of doxepin hydrochloride, capsaicin and a combination of both produces analgesia in chronic human neuropathic pain: a randomized, double—blind, placebo—controlled study." British journal of clinical pharmacology 49_6(2000): 574-579.
Nalamachu, Srinivas, et at. "A comparison of the lidocaine patch 5% vs naproxen 500 mg twice daily for the relief of pain associated with carpal tunnel syndrome: a 6-week, randomized, parallel-group study." Medscape General Medicine 8_3(2006): 33.
Delellis, Salvatore L, Dale H_Carnegie, and Thomas J_Burke_"Improved sensitivity in patients with peripheral neuropathy: effects of monochromatic infrared photo energy_"Journal of the American Podiatric Medical Association 952 (2005): 143-147.
Suekawa et at. "Pharmacological studies on ginger_1_ Pharmacological actions of pungent constitutents,(6)-gingerol and (6)-shogaoL"Journal ofpharmacobio-dynamics 7_11(1984): 836-848.
Vendruscolo et ai, Antiinflammatory and antinociceptive activities of zingiber officinale roscoe essential oil in experimental animal models, Ind J Pharm, vol. 38, No. 1, pp. 58-59, 2006.

(56) References Cited

OTHER PUBLICATIONS

Pittler et al., Temporary relief of postherpetic neuralgia pain with topical geranium oil, Am. J. Med., vol. 115, pp. 586-587, Nov. 2003.
Kalso, E Sodium Channel Blockers in Neuropathic Pain, Current Pharmaceutical Design, vol. 11, No. 23, Sep. 2005, pp. 3005-3011(7).
Sindrup, Soren H.; Otto, Marit; Finnerup, Nanna B. Jensen, Troels S.Antidepressants in the Treatment of Neuropathic Pain Basic & Clinical Pharmacology & Toxicology, vol. 96, No. 6, Jun. 2005, pp. 399-409(11).
Jensen TS. Anticonvulsants in neuropathic pain: rationale and clinical evidence. Eur J Pain. 2002;6 Suppl A:61-8.
Elon Eisenberg, MD; Ewan D. McNicol, RPh; Daniel B. Can, MD Efficacy and Safety of Opioid Agonists in the Treatment of Neuropathic Pain of Nonmalignant Origin JAMA. 2005;293:3043-3052.
Fromm GH. Baclofen as an adjuvant analgesic. J Pain Symptom Management 1994;9(8):500-509.
Eide K, Stubhaug A, Oye I, Breivik H. Continuous subcutaneous administration of the N-methyl-D-aspartic acid (NMDA) receptor antagonist ketamine in the treatment of postherpetic neuralgia. Pain 1995;61(2):221-8.
Sindrup SH, Jensen TS. Efficacy of pharmacological treatments of neuropathic pain: an update and effect related to mechanism of drug action. Pain 1999;83(3):389-400.
Kronenberg RH. Ketamine as an analgesic: parenteral, oral, rectal, subcutaneous, transdermal and intranasal administration. J Pain Palliat Care Pharmacother. 2002;16(3):27-35.
Greenway FL, Frome BM, Engels TM 3rd, McLellan A. Temporary relief of postherpetic neuralgia pain with topical geranium oil. Am J Med Nov. 2003; 115(7):586-7.

Nicoletta Galeotti, Lorenzo Di Cesare Mannelli, Gabriela Mazzanti,Alessandro Bartolini, Carla Ghelardini Menthol: a natural analgesic compound Neuroscience Letters 322 (2002) 145-148 Neurology 2005;65:812-819.
New Jersey Dept of Health Hazardous Substance Fact Sheet Jul. 1999 #0052.
Johnston, Gar. GABA Receptor Channel Pharmacology. Current Pharmaceutical Design 2005,11,1867-1885.
Jain et al., Essential oil composition of geranium (*Pelargonium* sp.) from the plains of Northern India, Flavour and Journal, 2001, pp. 44-46, John Wiley & Sons, Ltd.
Galeotti, Nicoletta et al., Local Anaesthetic Actvity of (+)- and (−)-Menthol, Planta Med 67, 2001, pp. 174-176, Georg Thieme Verlag Stuttgart, New York.
Rajeswara, Rao et al., History and botanical nomenclature of rose-scented geranium cultivars grown in India, ResearchGate, Jan. 1992, pp. 155-160.
Lai, Josephine et al., The role of voltage-gated sodium channels in neuropathic pain, Current Opinion in Neurobiology, 2003, pp. 291-297, Elsevier.
Jiro, Imanishi, For Stiff Shoulder or Pain, The Japanese Journal of Clinical Nursing, 2004, pp. 409-416.
A definition of "nociceptive" from a medical dictionary online available at http://medical-dictionary.thefreedictionary.com/nociceptive on Mar. 27, 2014.
Haiyan et al., Antinociceptive effects of matrine on neuropathic pain induced by chronic constriction injury, Pharm Biol. Jul. 2013;51(7):844-50, Epub Apr. 29, 2013 (Abstract).
Chang, Tao-Hsin, et al, "Structure of a heterotetrameric geranyl pyrophosphate synthase from mint (Mentha piperita) reveals intersubunit regulation." The Plant Cell 22.2 (2010): 454-467.
Anonymous, "Neuragen PN," https://web.archive.org/web/20080723165403/http://www.fottamerica.com/neuragenon.html, Jul. 23, 2008.

* cited by examiner

COMPOSITION AND METHOD FOR INHIBITION OF NERVE TRANSMISSION

CROSS REFERENCE TO RELATED APPLICATION

This application is a continuation of international application No. PCT/CA2008/000236, filed Feb. 6, 2008, and claims priority under 35 U.S.C. § 119(e) to U.S. provisional patent application No. 60/899,642, filed Feb. 6, 2007, both of which are incorporated herein in their entirety as though set forth explicitly herein.

FIELD OF THE INVENTION

The presently claimed and disclosed invention(s) pertains to the field of compositions comprising one or more aromatic terpene compound. More specifically, the presently claimed and disclosed invention(s) pertains to non-naturally occurring compositions comprising an aromatic terpene compound, and methods of using such compositions for the inhibition of nerve cell transmission.

BACKGROUND

Ideal physiological functioning requires an appropriate balance between nerve cell excitation and inhibition. Therefore, the identification of compounds, and methods of utilizing these compounds, to alter this balance, is of great interest and value.

It is well known that nociceptive pain and neuropathic pain are caused by different mechanisms, and therefore respond to different treatment modalities. Nociceptive pain is mediated by receptors which are located in skin, bone, connective tissue, muscle and viscera. These receptors typically respond to noxious chemical, thermal and mechanical stimuli producing pain that is typically described as sharp, aching, throbbing, or gnawing. In contrast, neuropathic pain is produced by damage to, or pathological changes in, the peripheral or central nervous systems, typically producing pain that is described as "burning", "electric", "tingling", and "shooting" in nature. In fact, neuropathic pain is most often diagnosed based on the symptoms, such that any pain that is characterized by burning sensations and/or shooting pain and/or numbness and/or tingling and/or allodynia is typically considered neuropathic. Other characteristics of neuropathic pain include hyperpathia (greatly exaggerated pain sensation to stimuli), hyperesthesia (an increased sensitivity to normal stimulation), dysesthesia (unpleasant abnormal sensations as if damage is being done when this is not the case), and paresthesia (an abnormal sensation, such as "pins and needles", whether spontaneous or evoked).

Nociceptive pain usually responds to opioids and nonsteroidal anti-inflammatories (NSAIDS), whereas the success of treating neuropathic pain with these approaches has been limited. Conversely, agents employed to treat neuropathic pain, such as gabapentin, have little or no effect on nociceptive pain.

Current conventional pharmacologic strategies for treating neuropathic pain follow a number of different approaches as outlined below:

Antiarrhythmics: Certain antiarrhythmics have sodium-blocking activity. Low-dose IV lidocaine is sometimes used for temporary pain relief from peripheral nervous system injuries, including diabetic neuropathy and postherpetic neuralgia. However, IV lidocaine therapy requires constant monitoring of the patient's ECG and blood pressure to decrease the risk for seizures and arrhythmias. (1)

Antidepressants: Both tricyclic antidepressants and serotonin reuptake inhibitors have been used to treat neuropathic pain. Numerous clinical trials demonstrate the safety and efficacy of TCAs when used to treat either diabetic neuropathy or postherpetic neuralgia, yet response rates have been low at approximately 33%. Amitriptyline was the first tricyclic used to treat neuropathy, and it is still widely prescribed. Amitriptyline has a high incidence of anticholinergic side effects, including delirium in elderly patients. TCAs also have proarrhythmic effects which limit their use in populations with abnormal EKG. Serotonin specific reuptake inhibitors (SSRIs) have demonstrated less consistent effects on neuropathic pain, relieving neuropathic pain in only one of seven patients. Serotonin noradrenaline reuptake inhibitors have fared slightly better with a response rate of one in every 4-5 neuropathic pain sufferers. (2)

Anticonvulsants: Carbamazepine, phenytoin, gabapentin and lamotrigine have all been used to treat neuropathic pain. Inhibition of sodium channel blocking activity by agents such as carbamazepine, phenytoin, and lamotrigine is the proposed mechanism. Studies have shown the anticonvulsant gabapentin to be effective in painful diabetic neuropathy, mixed neuropathies, and postherpetic neuralgia. The most common adverse effects of anticonvulsants in general are sedation and cerebellar symptoms (nystagmus, tremor and incoordination). The most common side effects associated with gabapentin are asthenia, headache, dizziness and somnolence, and in some cases polyneuropathy. Lamotrigine was no better than placebo when used to treat neuropathic pain other than trigeminal neuralgia. (3)

NSAIDS: NSAIDS are not generally recommended first-line agents for treating neuropathic pain. Relief of neuropathic pain with nonsteroidal anti-inflammatory drugs (NSAIDs) is variable. (4)

Opioids: Treatment of neuropathic pain has with opioids has been controversial. Opioids were thought to be ineffective for treating neuropathic pain, but may be somewhat effective for patients who have failed other modalities. Short-term studies provide only equivocal evidence regarding the efficacy of opioids in reducing the intensity of neuropathic pain, while intermediate-term studies demonstrate significant efficacy of opioids over placebo. Reported adverse events of opioids are common and long-term efficacy, safety (including addiction potential), and effects on quality of life need to be further evaluated. Overall, neuropathic pain may be less responsive to opioids than other types of pain. (5)

Other Agents: Baclofen, which blocks both presynaptic and postsynaptic GABA B receptors, is used as a first-line agent to treat trigeminal neuralgia. The most common side effect is drowsiness, and there is concern about possible addictive effects. (6)

Ketamine, an N-methyl-D-aspartic acid (NMDA) receptor antagonist, has garnered increased interest for treating neuropathic pain. Ketamine has been shown to relieve the symptoms of postherpetic neuralgia. However, ketamine causes sedation, slowed reaction times and hallucinations with long-term use. For this reason, it not currently recommended for use in chronic non-malignant pain. (7)

Dextromethorphan is also an NMDA antagonist. It has been used with some success to decrease pain in patients with diabetic neuropathy, but has not benefited those with postherpetic neuralgia, post stroke pain, or peripheral neuropathies other than diabetic. (8)

Topical Agents: Topical agents offer the advantage of local relief without systemic toxicity. Transdermal clonidine has been used with mixed results to treat diabetic neuropathy. Capsaicin cream, which contains an extract of chili peppers, is sometimes used to treat neuropathic pain. It may act on unmyelinated primary afferent nerves by depleting substance P. Depletion requires repeated and consistent use of capsaicin, and patient compliance can be an issue due to the common side effect of an intense burning sensation that decreases with consistent use. Overall, relief with capsaicin cream in clinical trials of neuropathic pain has been inconsistent. (4) Ketamine is a parenteral anesthetic agent that provides analgesic activity at sub-anesthetic doses. It is an N-methyl-D-aspartate (NMDA) receptor antagonist with opioid receptor activity. Controlled studies and case reports on transdermal ketamine demonstrate efficacy in neuropathic pain. (9) Geranium oil, a steam distillate of the geranium plant (*Pelargonium* spp) that is used in flavors and fragrances, is generally regarded as safe by the U.S. Food and Drug Administration. Topical application of geranium oil has been shown to relieve the pain of post-herpetic neuralgia in ⅔ subjects, with ¼ of subjects having a dramatic clinical response. (10)

Overall, the efficacy of these pharmacological treatments is often limited by side effects at the doses required for analgesia, as well as in some cases long delays before the onset of analgesia, a substantial rate of non responsiveness to therapy, and a potential for addiction. In conclusion, neuropathic pain does not have an ideal or even a very good treatment at the present time. A new and novel non-toxic topical or oral preparation to treat neuropathic pain is therefore of great interest and has the potential to benefit a wide range of chronic pain sufferers.

Natural substances provide a rich diversity of chemical structures, many of which have shown efficacy as therapeutic agents. In terms of inhibition of nerve function, a variety of classes of naturally derived compounds has shown the ability to inhibit neuronal firing by various methods, including affects on nerve cell receptors and associated ion channels. For example, flavanoids, terpenes, terpenoids, ginsenosides, and a variety of other dietary and environmental compounds have been shown to influence nerve transmission rates. (17)

Borneol, for instance, is a bicyclic monoterpene present in the essential oils of a number of medicinal plants, and has been shown to have a "highly efficacious" modulating action on nerve cell receptors. (18) Interestingly, traditional herbs containing borneol, such as *valerian officinalis, matricaria chamomilla*, and *lavandula officinalis*, have been used as sedatives to relieve anxiety, restlessness, insomnia and as analgesics. No other terpene has been previously found to have effect on nerve cell transmission.

In fact, many plant derived essential oils have been reported to have beneficial analgesic and anti-inflammatory properties for the treatment of nociceptive pain. For example, a number of species of ginger (*Zingiber* spp.) have been shown to consisting of monoterpenes (phellandrene, camphene, cineole, citral, and borneol), sesquiterpenes (zingiberene, zingiberol, zingiberenol, β-bisabolene, sesquiphellandrene, and others), aldehydes and alcohols. (11)

Menthol is a common and naturally occurring compound of botanical origin found in plants of the Mentha genus which has also been shown to possess analgesic properties with regard to nociceptive pain. (12) There has been, however, very little research into plant extracts for the treatment of neuropathic pain. One controlled trial of a Cannabis based extract given as an oromucosal spray (Sativex®, GW Pharmaceuticals, United Kingdom), however, did show benefit in centrally mediated neuropathic pain in 64 multiple sclerosis patients. (13)

Geranium oil has been used extensively in perfumery, as an insect repellent, and for other related purposes. For example, U.S. Pat. No. 4,940,583, Thompson, describes the use of geranium oil as a component in an animal repellent composition. U.S. Pat. No. 4,923,685, Forg et al., describes the use of geranium oil as part of a mouth wash composition. U.S. Pat. No. 4,579,677, Hooper et al., describes the use of geranium oil as a scenting agent in a bleaching composition. U.S. Pat. No. 4,311,617, Ansari et al., describes the use of geranium oil in perfumery compositions. United States Patent 5,260,313, Frome, entitled "Diagnosis and treatment of various neuralgias," relates to a method of diagnosing and treating neuropathic pain syndromes with a composition of which *Pelargonium graveolens* Ait. oil is the principle therapeutic agent. This essential oil distillate is alternatively called geranium oil, bourbon, oil geranium reunion, and oil rose-geranium.

The use of an essential oil distillate geranium oil, however, as taught by Frome, employs a complex mixture of naturally derived compounds, some of which may be effective for neuropathic pain relief and some which may be ineffective or which may be irritating or toxic. For example, a number of constituents found in natural geranium oil are known irritants and thereby may cause skin rash when applied topically or even exacerbate pain. For instance a-pinene, a constituent of natural geranium oil, is considered irritating to the skin and exposure can cause rash, burning pain, headache, vomiting and even kidney damage. (15) B-phellandrene has known hypersensitizing effects which can cause contact dermatitis. (16) P-cymene, another component of natural geranium oil, is also considered a "primary skin irritant", which can cause erythema upon contact and headache, nausea and vomiting if exposure is oral or inhaled. (17)

There remains a need for alternative therapies for inhibition of nerve cell transmission that do not suffer the drawbacks associated with existing pharmaceuticals, including essential oil distillates.

This background information is provided for the purpose of making known information believed by the applicant to be of possible relevance to the presently claimed and disclosed invention(s). No admission is necessarily intended, nor should be construed, that any of the preceding information constitutes prior art against the presently claimed and disclosed invention(s).

SUMMARY OF THE INVENTION

An object of the presently claimed and disclosed invention(s) is to provide a composition and method for the inhibition of nerve transmission. The presently claimed and disclosed invention(s) relates to a composition and method for the inhibition of nerve cell transmission. The composition and method of the presently claimed and disclosed invention(s) have wide ranging applications, such as, but not limited to, the development of therapeutic agents with analgesic, sedative, anxiolytic, anti-convulsant, hypnotic, muscle relaxant, anti-hypertensive, anti-depressant, and anti-psychotic properties.

In accordance with one aspect of the presently claimed and disclosed invention(s), there is provided a composition for the inhibition of nerve transmission comprising at least one terpene compound or a combination of terpene compounds and, optionally, one or more pharmaceutically acceptable diluents or excipients, wherein said terpene compound is not borneol.

In accordance with one aspect of the presently claimed and disclosed invention(s), there is provided a composition for treating neuropathic pain comprising at least one terpene compound or a combination of terpene compounds and, optionally, one or more pharmaceutically acceptable diluents or excipients.

In accordance with another aspect of the presently claimed and disclosed invention(s), there is provided a composition for the inhibition of nerve transmission comprising one or more compounds of Formula I or Formula II, or a pharmaceutically acceptable isomer, salt, ester or hydrate thereof,

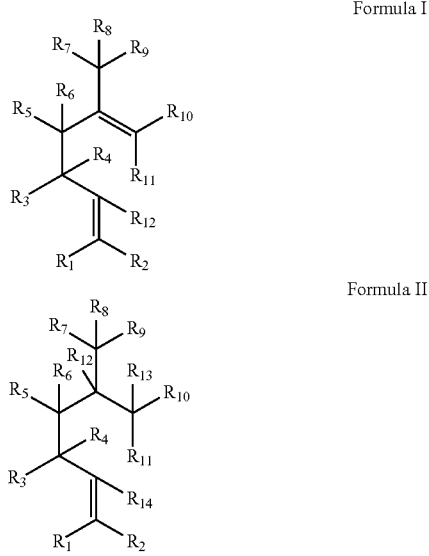

Formula I

Formula II wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, $COOCH_3$, $CH_2OH$, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_1$-$C_{20}$ unbranched allyl group and $C_1$-$C_{20}$ branched allyl group, or one or more of $R_3$ and $R_4$, $R_5$ and $R_6$, $R_7$ and $R_8$, or $R_{10}$ and $R_{11}$, together form =O, wherein the alkyl, alkoxy, acyloxy and allyl groups are optionally substituted with an aryl, amine, amide, halide, phosphate or thiols, and, optionally, one or more pharmaceutically acceptable diluent or excipient.

In accordance with another aspect of the presently claimed and disclosed invention(s), there is provided a method of treating a disorder characterized by an imbalance between nerve excitation and inhibition comprising administering a therapeutically effective amount of a composition as described herein to a mammalian subject, wherein said therapeutically effective amount is an amount that inhibits nerve cell transmission. The mammalian subject is preferably a human. Preferably, the method of the presently claimed and disclosed invention(s) is for the treatment of neuropathic pain, which can be caused by, for example, diabetic peripheral neuropathy, herpes zoster, post herpetic neuralgia, trigeminal neuralgia, complex regional pain syndrome, reflex sympathetic dystrophy, phantom limb syndrome, chronic disease (multiple sclerosis, HIV, etc), trauma (causalgia), impingement (e.g., sciatica, carpal tunnel, etc), drug exposure, toxic chemical exposure, current infection, past infection, impaired organ function, vascular disease, metabolic disease, cancer, cancer treatment, autoimmune disease, fibromyalgia, or it is idiopathic.

In one preferred embodiment of the presently claimed and disclosed invention(s) there is provided a method for the treatment of neuropathic pain by administering one or more terpene molecules, such as geraniol, citronellol and related compounds. In particular, the presently claimed and disclosed invention(s) provides a previously unavailable method for, in general, inhibiting nerve transmission, and in particular, treating a range of neuropathies, through the administration, usually topical or oral administration, to a mammal of a composition comprising one or more terpene moledules, such as geraniol, citronellol, or related compounds, alone or in combination.

DETAILED DESCRIPTION OF THE INVENTION

Figure 1:
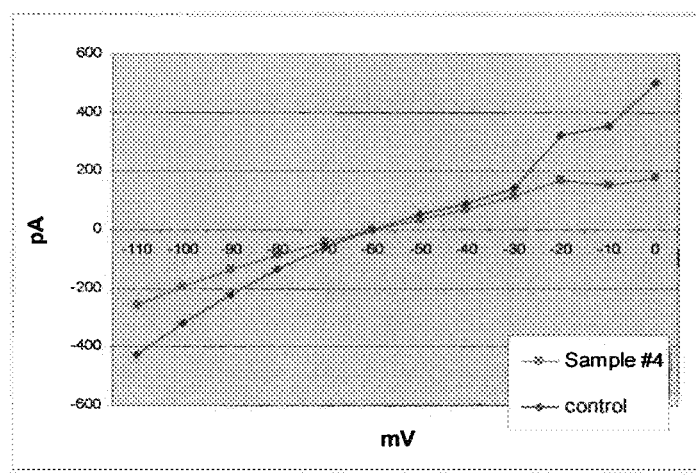
FIG. 1 depicts current-voltage plots obtained from patch clamp elecrophysiological studies of mouse hippocampal slices using sample #4 (Geraniol) and a Control, which demonstrate a reduction of membrane currents (geraniol vs. control).

Before explaining at least one embodiment of the presently claimed and disclosed invention(s) in detail, it is to be understood that the presently claimed and disclosed invention(s) is not limited in its application to the details of construction, experiments, exemplary data, and/or the arrangement of the components set forth in the following description or illustrated in the drawings. The presently claimed and disclosed invention(s) is capable of other embodiments or of being practiced or carried out in various ways. Also, it is to be understood that the phraseology and terminology employed herein is for purpose of description and should not be regarded as limiting.

The presently claimed and disclosed invention(s) overcomes many of the limitations and drawbacks associated with the prior use of essential oil distillates. By employing isolated and/or purified compounds, and compositions thereof, which are responsible for the inhibition of nerve transmission, the desired effect can be better controlled and enhanced than when the same compounds are present in an unpurified form in a natural oil distillate. Therapeutic agents can therefore be better designed and the quality of these agents controlled by standardizing to the known active ingredients. Compounds that are ineffective, irritating or toxic can be excluded from such synthetic compositions. Furthermore, the use of synthetically derived versions of these compounds are more economical to acquire and supply is not affected by climatic conditions or severe weather that often affects medicinal plant production.

The presently claimed and disclosed invention(s) provides a previously unavailable and novel means of restoring balance between nerve excitation and inhibition by the administration of a composition comprising a compound or mixture of compounds that inhibit nerve transmission. The composition of the presently claimed and disclosed invention(s) comprises at least one terpene compound, or a pharmaceutically acceptable salt, ester or solvate thereof, and, optionally, a pharmaceutically acceptable diluent or carrier.

As used herein, the term "terpene compound" is intended to refer to a terpene, a terpenoid, or a pharmaceutically acceptable is salt, ester or solvate thereof. A "terpenoid" is a chemically modified terpene. Examples of terpenoids include, but are not limited to, terpenoid aldehydes, terpenoid acids, terpenoid esters and terpenoid oxides.

In accordance with a specific embodiment of the presently claimed and disclosed invention(s), the terpene compound in the composition is geraniol, citronellol, geranial, citronellal, linalool, menthone, rose oxide, alpha-terpineol, a pharmaceutically acceptable is salt, ester or solvate thereof, or any mixture thereof.

Preferably the terpene compound has the structure of Formula I or II,

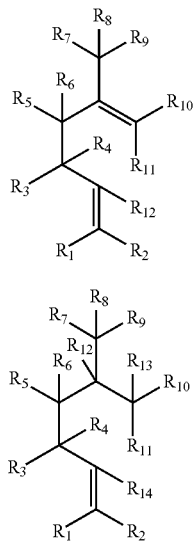

Formula I

Formula II where, $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_3$-$C_{20}$ unbranched allyl group and $C_3$-$C_{20}$ branched allyl group, or one or more of $R_3$ and $R_4$, $R_5$ and $R_6$, $R_7$, and $R_8$, and $R_{10}$ and $R_{11}$, is =O.

wherein the alkyl, alkoxy, acyloxy and allyl groups are optionally substituted with one or more aryl groups, amine groups, amide groups, halides, phosphate groups or thiols.

In accordance with another embodiment of the composition comprises a compound of Formula I or II, wherein $R_1$, $R_2$, $R_3$, $R_4$, $R_5$, $R_6$, $R_7$, $R_8$, $R_9$, $R_{10}$, $R_{11}$, $R_{13}$ and $R_{14}$ are independently selected from H, OH, COOH, COOCH$_3$, CH$_2$OH, OCOH, $C_1$-$C_{10}$ unbranched alkyl group, $C_1$-$C_{10}$ branched alkyl group, $C_1$-$C_{10}$ unbranched alkoxy group, $C_1$-$C_{10}$ branched alkoxy group, $C_1$-$C_{10}$ unbranched acyloxy group and $C_1$-$C_{10}$ branched acyloxy group, $C_3$-$C_{10}$ unbranched allyl group and $C_3$-$C_{10}$ branched allyl group, or one or more of $R_3$ and $R_4$, $R_5$ and $R_6$, $R_7$, and $R_8$, and $R_{10}$ and $R_{11}$, is =O.

In accordance with another embodiment of the composition comprises a compound of Formula I or II, wherein $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently selected from H, OH, COOH, COOCH$_3$, CH$_2$OH, OCOH, $C_1$-$C_5$ unbranched alkyl group, $C_1$-$C_5$ branched alkyl group, $C_1$-$C_5$ unbranched alkoxy group, $C_1$-$C_5$ branched alkoxy group, $C_1$-$C_5$ unbranched acyloxy group and $C_1$-$C_5$ branched acyloxy group, $C_3$-$C_5$ unbranched allyl group and $C_3$-$C_5$ branched allyl group, or one or more of $R_3$ and $R_4$, $R_5$ and $R_6$, $R_7$, and $R_8$, and $R_{10}$ and $R_{11}$, is =O.

In accordance with another embodiment of the composition comprises a compound of Formula I, wherein $R_1$, $R_2$, $R_3$, $R_4$, $R_5$, $R_6$, $R_7$, $R_8$, $R_9$ and $R_{12}$ are H and $R_{10}$ and/or $R_{11}$ is selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_1$-$C_{20}$ unbranched allyl group and $C_1$-$C_{20}$ branched allyl group or $R_{10}$ and $R_{11}$ are together =O.

In accordance with a related embodiment, the composition comprises one or more compound of Formula I, which is:

geranial(3,7-dimethyl -2,6-octadienal),
neral(cis 3,7-dimethyl -2,6-octadienal),
geraniol(2,6-Octadien-1-ol, 3,7-dimethyl-, (2E)-),
nerol(cis-3,7-dimethyl-2,6,-octadien-1-ol),
geranyl formate(2,6-Octadien-1-ol, 3,7-dimethyl-, formate, (2E)-),
geranyl butyrate(Butanoic acid, (2E)-3,7-dimethyl-2,6-octadienyl ester),
geranyl tiglate(2-Butenoic acid, 2-methyl-, (2E)-3,7-dimethyl-2,6-octadienyl ester,(2E)-), or
a pharmaceutically acceptable isomer, salt, ester or solvate thereof.

In accordance with one embodiment of the composition comprises a compound of Formula 2, wherein $R_1$, $R_2$, $R_3$, $R_4$, $R_5$, $R_6$, $R_7$, $R_8$, $R_9$, $R_{12}$, $R_{13}$ and $R_{14}$, are H and $R_{10}$ and/or $R_{11}$ is selected from H, OH, COOH, COOCH$_3$, CH$_2$OH, OCOH, $C_1$-$C_{20}$ unbranched alkyl group, $C_1$-$C_{20}$ branched alkyl group, $C_1$-$C_{20}$ unbranched alkoxy group, $C_1$-$C_{20}$ branched alkoxy group, $C_1$-$C_{20}$ unbranched acyloxy group and $C_1$-$C_{20}$ branched acyloxy group, $C_1$-$C_{20}$ unbranched allyl group and $C_1$-$C_{20}$ branched allyl group or $R_{10}$ and $R_{11}$ are together =O.

In accordance with a related embodiment, the composition comprises one or more compound of Formula II, which is citronellal(3,7-dimethy-6-octen-1-al),
citronellol(3,7-dimethyloct-6-en-1-ol),
citronellyl formate(6-Octen-1-ol, 3,7-dimethyl-, formate), citronellyl butyrate(butanoic acid, 3,7-dimethyl-6-octenyl ester), citronellyl tiglate(2-Butenoic acid, 2-methyl-, 3,7-dimethyl-6-octenyl ester, (2E)-), or a pharmaceutically acceptable isomer, salts, ester or solvate thereof.

Specific examples of terpene compounds that can be incorporated in the compositions of the presently claimed and disclosed invention(s), alone or in combination, are geraniol(2,6-Octadien-1-ol, 3,7-dimethyl-, (2E)-), citronellol(6-Octen-1-ol, 3,7-dimethyl-, (2E)-), and their derivatives. These compounds have now been shown to effectively inhibit nerve transmission in both animal cortical nerve cells and dorsal root ganglion cells.

The terpene compounds of Formula I and Formula II have been found to be useful in treating the often unbearable and untreatable pain known as neuropathic pain, which is believed to be caused by aberrant nerve transmission due to damage to nerve tissue. The presently claimed and disclosed invention(s) describes a method of treating neuropathic pain using any of a class of aromatic terpene compounds, some of which can be found naturally occurring in *Pelargonium graveolens* Ait. essential oil or other plant sources, or which can be prepared synthetically. In particular, this invention discloses the class and structures of those terpene compounds which can be used to treat neuropathic pain. The presently claimed and disclosed invention(s) thereby provides previously unavailable information regarding the active constituents found in *Pelargonium graveolens* Ait. oil, other possible related plant species, as well as can be found in synthetic commercial essential oil blends, and those related compounds which can be synthesized chemically by one skilled in the art. The identification of these purified compounds represents an inventive step over U.S. Pat. No. 5,260,313 and other related references, and is not readily obvious to one skilled in the art.

It is well known that essential oils are complex mixtures of aromatic compounds comprising a broad range of molecular structures including both carbon rings or chains with or without double bonding and with a range of functional side groups. A typical plant essential oil chromatogram may contain in the order of 200 or more distinct peaks. Plant essential oils are a complex mixture of terpenes, sesquiterpenes, esters, alcohols, phenols, aldehydes, ketones, organic acids, and various miscellaneous molecular structures. Furthermore, each class of compound above contains many subclasses. For example, the terpene classification includes hemiterpenes, monoterpenes, diterpenes, sesquiterpenes, triterpenes, tetraterpenes, and associated terpenoids formed by the modification or oxidation of the carbon skeleton. Moreover, any of these compounds may have a wide range of physiological activity in a mammal, and in some cases may show adverse effects or toxicity if applied topically or administered orally. Due to this wide diversity, some of the compounds may even inhibit the effect of nerve transmission inhibition, or may cause an excitation of nerve transmission. Due to the wide range of compounds present, and the extreme complexity of receptor channel pharmacology, it is not obvious to one skilled in the art which compounds have desirable or undesirable effects on nerve transmission.

Therefore, in terms of pain relief, for example, it would not have been obvious to one skilled in the art, having regard to the previous use of essential oil distillates, which compounds within previous essential oil distillates inhibit pain, have no effect on pain, or even exacerbate pain. To determine which compounds are efficacious requires extensive research both on live mammalian subjects and live cell cultures of neuronal tissue in order to determine which (if any) compounds provide a therapeutic effect either singly or in combination.

Furthermore, since the mechanism of neuropathic pain development and the mechanism of relief of neuropathic pain are not well understood, it is not obvious to one skilled in the art as to which compounds would have the most effect on the relief of neuropathic pain, which compounds may inhibit the relief of neuropathic pain, or which compounds may have potential toxicity. It is therefore possible, but not obvious, that identification, purification, and testing of specific compounds found in essential oils may elucidate those compounds responsible for the relief of neuropathic pain. Also, in many well documented instances, the elucidation of active drug compounds from medicinal plants is not possible. One common reason for these failed attempts is that the physiological affect of the heterogeneous mixture of compounds found in the naturally derived plant extract or whole plant achieves its effects due to a synergy of compounds. Successive attempts to fractionate heterogeneous mixtures and elucidate one or more distinct active ingredients therefore fail because the synergistic effects of the complex mixture are lost. This phenomenon also supports the non-obviousness of the presently claimed and disclosed invention(s).

In developing the compositions and methods of the presently claimed and disclosed invention(s), extensive research was carried out using both in vitro and in vivo methods, with the goal of determining the active constituents found in geranium oil and/or other natural and synthetic aromatic oil sources which have a beneficial effect on nerve transmission. Geranium oil is composed of an abundance of chemical entities, many of which are known, but some of which are not yet elucidated (Table 1). In an effort to determine the active ingredient, or ingredients, in geranium oil, a synthetic blend was provided, which contains known amounts of compounds present in naturally-derived geranium oil (Table 1), and tested in a patch clamp assay (see Example 1). This synthetic geranium oil was then compared to the naturally-derived geranium oil. The synthetic geranium oil gave a 50% inhibition of current compared to a 40% inhibition for naturally-derived geranium oil. Thus, a synthetic blend of geranium oil had a greater activity than the naturally derived geranium oil, indicating that synthetically derived terpenes are superior.

Individual purified compounds contained within geranium oil were then tested both in vivo and in vitro. Specifically, whole cell patch clamp testing revealed that specific compounds found in geranium oil inhibited delayed rectifying potassium channels at a concentration of 10 ppm. Results were positive for the compounds carvone, linalool, terpineol, rose oxide, menthone, geraniol, and citronellol, with purified geraniol and purified citronellol giving the highest amount of inhibition.

A synthetic blend of geranium oil (Table 1) was also tested in a panel of human neuropathic pain sufferers known to respond to naturally derived geranium oil. The geranium oil was topically applied in therapeutically effective amounts to areas of the human body affected with symptoms of neuropathic pain. Dosage amounts depended on the size of the patient's affected areas. Typically, 1-10 drops were used, 1 drop for smaller affected areas and 10 drops with larger affected areas or areas exhibiting more severe pain symptoms. Once administered, a typical positive response is a significant reduction in pain, often in minutes. A significant number of patients in the panel of neuropathic pain sufferers preferred the pain relieving effects of the synthetic blend of geranium oil, with known purified constituents, over the natural geranium oil. This indicates that the synthetic geranium oil blends of the presently claimed and disclosed invention(s) offer improved efficacy over natural geranium oil.

To further investigate the effectiveness of the synthetic geranium oil blend, a human double blind placebo controlled clinical trial was carried out with 64 subjects suffering from all-cause neuropathic pain. Two active medications and one placebo were studied over a six week period. Each active medication contained approximately 28% by volume of geranium essential oil. One of these active medications contained the naturally derived essential oil of *pelargonium* spp., and the other contained an equal proportion of the synthetic geranium oil blend detailed in Table 1. As set out in Example 3 (and shown in Table 2), the active medication containing the synthetic oil blend resulted in statistically significant pain reduction in 95% of patients vs. 85% of patients using the naturally derived essential oil. In addition, this trial demonstrated pain reduction of significantly longer duration (7.5 hrs vs. 6.5 hrs) following treatment application of the synthetic blend vs. the naturally derived active medication.

TABLE 1

Components of synthetic oil compared to Geranium oil bourbon
(Analyzed by gas chromatography on DB-5 column.)

| Component | % in Synthetic Blend | % in Geranium Oil Bourbon |
| --- | --- | --- |
| cis hex-3-en-1-ol | 0.31 | 0.00 |
| linalool | 6.41 | 10.23 |
| phenylethyl alcohol | 0.88 | 0.00 |
| rose oxide, tr | 1.69 | 0.52 |
| menthone | 0.63 | 0.76 |
| isomenthone | 4.38 | 7.53 |
| borneol | 0.93 | 0.00 |
| a-terpineol | 0.96 | 1.01 |
| nerol | 1.55 | 0.63 |
| citronellol | 27.17 | 19.89 |
| neral | 0.25 | 0.42 |
| geraniol | 23.11 | 18.00 |
| linalyl acetate | 0.63 | 0.00 |
| geranial | 0.54 | 0.65 |
| citronellyl formate | 6.63 | 8.30 |
| neryl formate | 0.42 | 0.00 |
| geranyl formate | 5.50 | 6.77 |
| furanoperlargone A | 0.35 | 0.00 |
| geranyl tiglate | 15.00 | 1.25 |
| a-thujene | | 0.11 |
| a-pinene | | 0.94 |
| sabinene | | 0.09 |
| b-pinene | | 0.66 |
| myrcene | | 0.34 |
| a-phellandrene | | 0.11 |
| a-terpinene | | 1.00 |
| p-cymene | | 1.32 |
| limonene | | 4.47 |
| b-phellandrene | | 12.43 |
| benzyl alcohol | | 0.07 |
| cis-b-ocimene | | 0.19 |
| trans-b-ocimene | | 0.13 |
| g-terpinene | | 0.49 |
| terpinolene | | 2.54 |
| camphor | | 0.56 |
| terpin-1-en-4-ol | | 6.48 |
| lavandulyl acetate | | 0.14 |
| geranyl acetate | | 0.35 |
| b-caryophyllene | | 0.95 |
| a-guaiene | | 0.22 |
| aromadendrene | | 1.46 |
| 6,9-guaiadiene | | 0.33 |
| geranyl propionate | | 0.29 |

TABLE 1-continued

Components of synthetic oil compared to Geranium oil bourbon
(Analyzed by gas chromatography on DB-5 column.)

| Component | % in Synthetic Blend | % in Geranium Oil Bourbon |
| --- | --- | --- |
| germacrene D | | 0.17 |
| bicyclogermacrene | | 0.07 |
| b-bisabolene | | 0.06 |
| g-cadinene | | 0.08 |
| geranyl isobutyrate | | 0.32 |
| d-cadinene | | 0.33 |
| geranyl butyrate | | 0.14 |
| furanopelargone A | | 2.67 |
| phthalate ester | | 1.31 |
| unidentified | | 0.88 |
| unidentified | | 1.17 |
| unidentified | | 0.89 |
| unidentified | | 0.96 |
| % Total | 97.34 | 92.84 |

Further testing was carried out on human neuropathic pain sufferers using geraniol(2,6-Octadien-1-ol, 3,7-dimethyl-, (2E)-). Results indicated that pure, synthetically produced geraniol, provided almost immediate pain relief. As demonstrated by this activity of geraniol, this class of compounds has beneficial activity for the relief of neuropathic pain. Individual chemical entities in this class include, but are not limited to geraniol(2,6-Octadien-1-ol, 3,7-dimethyl-, (2E)-), geraniol(3,7-dimethyl -2,6-octadienal), geranyl formate(2,6-Octadien-1-ol, 3,7-dimethyl-, formate, (2E)-), geranyl tiglate(2-Butenoic acid, 2-methyl-, (2E)-3,7-dimethyl-2,6-octadienyl ester, (2E)-), geranyl butyrate(Butanoic acid, (2E)-3,7-dimethyl-2,6-octadienyl ester), citronellol(3, 7-dimethyloct-6-en-1-ol), citronellyl formate(6-Octen-1-ol, 3,7-dimethyl-, formate), citronellal(3,7-dimethy-6-octen-1-al), citronellyl butyrate(butanoic acid, 3,7-dimethyl-6-octenyl ester), and citronellyl tiglate(2-Butenoic acid, 2-methyl-, 3,7-dimethyl-6-octenyl ester, (2E)-).

Studies were also conducted on dissociated rat Dorsal Root Ganglion (DRG) neurons and mouse hippocampal brain slice preparations (Example 5). Mean current-voltage plots for 6 cortical neurons are shown in FIG. 1. Note the reduction of membrane currents in presence of pure geraniol, representing an inhibition of nerve transmission.

The results of in vitro studies and human clinical trials described above and detailed in the Examples, demonstrate that the synthetic compositions comprising geraniol and citronellol, and related terpenes of Formula I or II, have a significant effect on the inhibition of nerve transmission. For example, the synthetic compositions of the presently claimed and disclosed invention(s) have been found to be useful in treating neuropathic pain. Preferably, the composition contains geraniol and/or citronellol. The synthetic compositions comprising individual terpene compounds are more effective than the whole essential oil distillate. This is apparent from the in vitro and in vivo research Examples. Thus, a novel composition of purified terpenes of Formula I or II, for example, geraniol and citronellol and/or their derivatives, used alone or in combination, is effective as an inhibitor of nerve transmission and, in one preferred embodiment of the presently claimed and disclosed invention(s), is effective in the treatment of neuropathic pain.

A wide variety of physiologically undesirable states and frank medical pathologies have been generally accepted to be the result of imbalances between nerve excitation and inhibition in mammalian subjects. For instance, disorders of mood and sleep, such as insomnia, anxiety, restlessness, depression, cognitive disorders, schizophrenia, addictions, post traumatic stress disorder (PTSD) and disturbances of learning and memory have been associated with excess excitation of neuronal firing. This excess firing has also been associated with a wide variety of neurological conditions, some examples being restless leg syndrome, seizures, epilepsy, tremors, Huntington's disease, attention deficit disorder, autism and Tourettes's syndrome.

An imbalance between excitation and inhibition of the nerves is also known to be involved in various musculoskeletal disorders such as muscle spasm, inflammation and pain.

Thus, the compositions of the presently claimed and disclosed invention(s), which show inhibition of nerve cell transmission, have wide ranging applications. These applications include, but are not limited to, use as analgesics, anesthetics, anti-convulsants, anxiolytics, sedatives, hypnotics, muscle relaxants, anti-hypertensives, anti-depressants, anti-psychotics, etc.

One aspect of the presently claimed and disclosed invention(s) provides methods of treating neuropathic pain in mammalian subjects by administering a therapeutically effective amount of a composition comprising a terpene compound of Formula I or II, for example, geraniol and/or citronellol. Neuropathic pain is pain caused by various types of nerve damage. Some examples of neuropathic pain conditions that can be treated by the method of the presently claimed and disclosed invention(s) include, but are not limited to, diabetic peripheral neuropathy, herpes zoster, post herpetic neuralgia, trigeminal neuralgia, complex regional pain syndrome, reflex sympathetic dystrophy, migraine headache, phantom limb syndrome, neuropathic pain due to chronic disease (multiple sclerosis, HIV, etc), neuropathic pain due to trauma (causalgia), neuropathic pain due to impingement (i.e. sciatica, carpal tunnel, etc.), neuropathic pain due to drug exposure or toxic chemical exposure, neuropathic pain due to infection or post infection, neuropathic pain due to impaired organ function, neuropathic pain due to vascular disease, neuropathic pain due to metabolic disease, neuropathic pain due to cancer or cancer treatment, neuropathic pain due to autoimmune disease, neuropathic pain due to fibromyalgia, and neuropathic pain with no know cause (idiopathic).

The pharmaceutical compositions of the presently claimed and disclosed invention(s) can be prepared using standard, well known techniques. The pharmaceutical compositions of the presently claimed and disclosed invention(s) do not necessarily require inclusion of any pharmaceutically acceptable diluent or excipient. However, such diluents or excipients can be incorporated into the composition as required depending on the desired characteristics of the composition. As used herein, the term "composition" can refer to a pharmaceutical preparation containing a terpene compound alone.

The compositions of the presently claimed and disclosed invention(s) are prepared using isolated or purified terpene compounds, for example, one or more compounds of Formula I or II, or corresponding pharmaceutically acceptable salts, esters or solvates thereof as active components. The term "solvate" is intended to include "hydrate". The compositions of the presently claimed and disclosed invention(s) are not natural oils derived as distillates of plant material, however, the terpene compounds used to prepare the synthetic compositions of the presently claimed and disclosed invention(s) can include one or more compounds that have been isolated from plant material.

The compositions of the presently claimed and disclosed invention(s) can be prepared and administered in a wide variety of dosage forms. The composition of the presently claimed and disclosed invention(s) can be in the form of a suspension, pill, gel, oil, cream, patch, spray or aerosol. The composition can be formulated to be suitable for oral administration, topical administration, intranasal delivery, transdermal administration. It will be obvious to those skilled in the art that the following dosage forms can comprise as the active component, a compound of Formula I or II, a corresponding pharmaceutically acceptable salt, ester or solvate thereof, or any combination thereof.

For preparing pharmaceutical compositions from the compounds of the presently claimed and disclosed invention(s), pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

A particularly preferred mode of administration of the composition of the presently claimed and disclosed invention(s) is to a skin surface via a topical route. Such a composition is topically applied in the form of a lotion, solution, cream, ointment or powder. For example, the composition can be formulated into a cream consisting of an aqueous emulsion of polyethylene glycols or liquid paraffin or can be incorporated at a concentration between 1 and 10% into an ointment consisting of a white wax or white soft paraffin base together with such stabilizers and preservatives as may be required. The topical compositions can contain additional ingredients such as binders, excipients, antioxidants, and dyes.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted creams, lotions, ointments, tablets, capsules, or powders in tubes, vials or ampoules. Also, the unit dosage form can be a capsules, tablet, cachet, or lozenge itself, or it can be the appropriate number of any of these in packaged form.

The quantity of active component in a unit dose preparation may be varied or adjusted according to the particular application and the potency of the active component. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

To gain a better understanding of the presently claimed and disclosed invention(s) described herein, the following examples are set forth. It should be understood that these examples are for illustrative purposes only. Therefore, they should not limit the scope of the presently claimed and disclosed invention(s) in any way.

EXAMPLES

Example 1

Patch Clamp Electrophysiological recordings (K+ Channels

Potassium channels have been associated with a number of important cellular functions including the regulation of heart rate, muscle contraction, neurotransmitter release, and neuronal excitability (14). As such, K+ channels have been recognized as potential drug targets and have been utilized as screening agents for potential therapeutic molecules, including potential therapeutic drugs for pain. The role of K+ channels in controlling cell membrane potential and neuronal cellular excitability makes them of interest in modulating neruronal hyperexcitability states, including neuropathic pain.

Whole cell patch clamp recordings (Axopatch 200B) were made using borosilicate patch pipettes of resistance 3-8 MΩ with an intracellular solution utilizing potassium chloride as the current carrier. Current clamp recording were conducted holding the membrane potential at −60 mV to characterize the firing property of the cells. Voltage clamp was performed to investigate the delayed rectifier current (Ikv), specifically Ikv 1.5 subtype. Statistical significance was assessed using ANOVA followed by Duncan's multiple-range test with $P<0.05$ taken as indicating significance. Geranium oil was found to inhibit the delayed rectifying potassium channel at 10 mcmol or 10 ppm, and the $EC_{50}$ of geranium oil was 5.4 ppm. At a concentration of Geranium oil that gave 40% inhibition of the delayed rectifier potassium current, the following components of geranium oil gave these corresponding percent inhibitions: Carvone 22%, Linalool 18%, Terpineol 14%, Rose Oxide 14%, Menthone 22%, Geraniol 26%, and Citronellol 27%. A synthetic blend of geranium oil containing proportions of geraniol and citronellol similar to natural geranium oil, but with other components removed, was compared to the following ratios of geraniol:citronellol; 2:8, 3:7, 4:6 and geranium oil. The synthetic blend of geranium oil gave a 50% inhibition of the delayed rectifying potassium channel current compared to a 40% inhibition for natural geranium oil. All ratios of geraniol:citronellol tested also significantly inhibited these channels.

The finding that a synthetic blend of geranium oil was superior to geranium oil of plant origin is very significant. Geranium oil from natural sources contains approximately 50 individual gas chromatography peaks with at least 6% of chemical compounds that are difficult to identify. It would be very difficult to isolate active ingredients from this mix given the number of constituents and the number of unidentified components found in geranium from plant origin. By comparison, a synthetic blend of geranium oil can be used, in this case containing only 19 constituents, all of which are known chemical entities. Also of significance is the result that of all the individual compounds tested, geraniol and citronellol showed the highest activity in the patch clamp testing. Furthermore, purified geraniol and purified citronellol, at various ratios, also showed a high degree of efficacy in these tests.

Example 2

Human Screening Using Synthetic Geranium in Neuropathic Pain (Post-Herpetic Neuralgia)

Since natural geranium oil relieves neuropathic pain and inhibits the delayed rectifying potassium channel, and since synthetic geranium oil, geraniol, and citronellol all inhibit the delayed rectifying potassium channel, synthetic geranium oil and geraniol were tested on patients with post-herpetic neuralgia. A synthetic blend of geranium oil was tested in patients with post-herpetic neuralgia that were positive responders to natural geranium oil. Pain relief with a synthetic blend of geranium oil (see Table 1 for constituents their relative amounts in the synthetic blend) was self reported to be as good or better than pain relief with natural geranium oil. Pure geraniol was then tested in these subjects. Results indicated that geraniol had the greatest effect on neuropathic pain relief.

Example 3

Human Clinical Trial of 64 Patients with all Cause Neuropathy

A total of 64 individuals with diagnosed peripheral neuropathy of at least 3 months duration and experiencing daily plantar cutaneous foot pain were recruited and screened for eligibility. Of these individuals, 18 were excluded because they did not meet the predetermined inclusion criteria for foot pain (VAS=3-8). The remaining participants completed three weeks of pain-relieving intervention as described below. One participant did not complete the intervention due to unknown reasons. Of those participants that competed all testing procedures (n=45), five participants reported pre-test foot pain levels outside of the predetermined criteria (VAS <3 or >8) at least once throughout the study period. All data acquired from these participants was excluded from subsequent analyses. There was no adverse event during the study period to report.

Pain was recorded before treatment and for 8 hrs after treatment on an 11 point (0-10) numeric scale. One of three treatments (synthetic geranium oil (see Table 1), placebo, and naturally-derived geranium oil) was randomly applied to all subjects in a repeatable fashion according to predetermined application instructions. A one week wash out period was maintained between each application. Each active medication contained approximately 28% by volume of geranium essential oil in a topical cream. One of these active medications contained the naturally derived essential oil of *pelargonium* spp., and the other contained an equal proportion of the synthetic geranium oil blend detailed in Table 1.

Forty participants completed all pain reduction testing (men=16, women=24, age=71.5±1.5 years, height=171.0±1.8 cm, body mass=80.6±21.0 kg, PN duration since diagnosis=6.63±0.70 years). Causes of PN were diabetes (n=16), chemotherapy (n=4) and unknown cause (n=20). Inputted pain scale data were downloaded to a computer and analyzed at a later time. Two-factor (Time and Treatment) analyses of variance with repeated measures (ANOVA) were used for data analysis. Tukey post-hoc analysis was employed whenever necessary. Significance level was set at alpha=0.05. The immediate pain reduction effects were evaluated by comparing pain level (VAS) 30 minutes before (i.e., Pre) and after (i.e., Post) the treatment applications. There was no statistical difference in pain levels before the treatment applications. Each treatment had different pain relieving effects (see Table 1). As shown in Table 3, the active medication containing the synthetic oil blend resulted in statistically significant pain reduction in 95% of patients vs. 85% of patients using the naturally derived essential oil. In addition, this trial demonstrated pain reduction of significantly longer duration (7.5 hrs vs. 6.5 hrs) following treatment application of the synthetic blend vs. the naturally derived active medication.

TABLE 2

Summary of pain relieving effects of three treatments

| | Reduced Pain | | | No Change | | | Pain Increase | | |
|---|---|---|---|---|---|---|---|---|---|
| | N | % | Mean ΔVAS | N | % | Mean ΔVAS | N | % | Mean ΔVAS |
| Synthetic | 38 | 95 | −2.74 | 1 | 3 | 0 | 1 | 3 | +3 |
| Placebo | 23 | 58 | −2.13 | 13 | 32 | 0 | 4 | 10 | +1.5 |
| Natural | 34 | 85 | −2.82 | 6 | 15 | 0 | 0 | 0 | 0 |

Example 4

Case Study 77 yo Caucasian male, Ht 68 inches, Weight 162 lb. BMI 24.7. History of shingles 4 years prior to study with residual pain (post herpetic neuralgia). The subject tried Neurontin™ (Pfizer, U.S.) for 1 week with only some help and quit 3-4 years prior to this study.

He had moderate pain that made it hard to concentrate on things other than the pain. He did not want to wear clothing and felt uncomfortable most of the time. He could sleep, but had to keep changing positions to do so. He described the post-herpetic neuralgia as the worst thing to have happened to him. The subject's pain decreased by 78% with pure geraniol over the course of 30 minutes after topical application as measured on a standard visual analog scale.

Example 5

Patch Clamp Electrophysiological Studies of Mouse Hippocampal Slices

Studies were conducted on mouse hippocampal brain slice preparations. In terms of the slice preparations, 200-400 μM coronal brain slices were prepared from animals housed in a 12 hour light (ZT 0-12):12 hour dark (ZT 12-24) environment. Animals were anesthetized with isoflurane, decapitated, the brain rapidly removed and placed in ice cold, oxygenated (95% $O_2$:5% $CO_2$), bicarbonate-buffered artificial cerebral spinal fluid (ACSF). A 1 $cm^2$ block of brain tissue containing the hippocampi was glued to a cutting surface and coronal slices were prepared using a Leica VT1000S microtome (Leica Microsystems). All slices were left to equilibrate for approximately one hour prior to the transfer to a recording chamber. Once transferred to the chamber, slices were continuously superfused with oxygenated ACSF at a rate of 3 ml/min @30° C. and recordings are generally made for the next 6-12 hours. Patch microelectrodes (5-8MΩ) made from borosilicate glass (Garner Glass Co.) and filled with $K^+$based internal patch solution composed of: (in mM) 120 K-acetate, 40 HEPES, 10 EGTA, 6 $MgCl_2$, nystatin (450 μg/ml) or gramicidin B (5 μg/ml) and pluronic acid F127.

The perforated patch recording technique and will be used (Korn & Horn, 1989) and viable Hippocampal neurons were visually targeted using Infrared Differential Interference Contrast (IR-DIC) microscopy using a Leica DM LFSA scope. The perforated patch configuration provides access resistances to the cell comparable to conventional whole cell recordings and such access is generally obtained 2-15 minutes after gigaohm seals are formed. Recordings were made from 3 different patch rigs equipped with either Axopatch 700B patch clamp amplifiers interfaced via a Digidata 1322A to a PC computer or on, in terms of the studies performed on dissociated DRG neurons, a Zeiss Axoscop 200 inverted microscope equipped with an Axopatch 200B/Digidata 1322A using Pclamp 9.0 and Axoscope 9 software.

Test compounds were bath-applied by superfusion to examine for changes in excitability and/or attenuation of ion channels and the effects of compounds on evoked synaptic responses. Stimulating electrodes (concentric or bipolar) were placed within the slices and in accordance with the well known fiber tract pathways of passage for the DH and the hippocampus.

Figure 2:
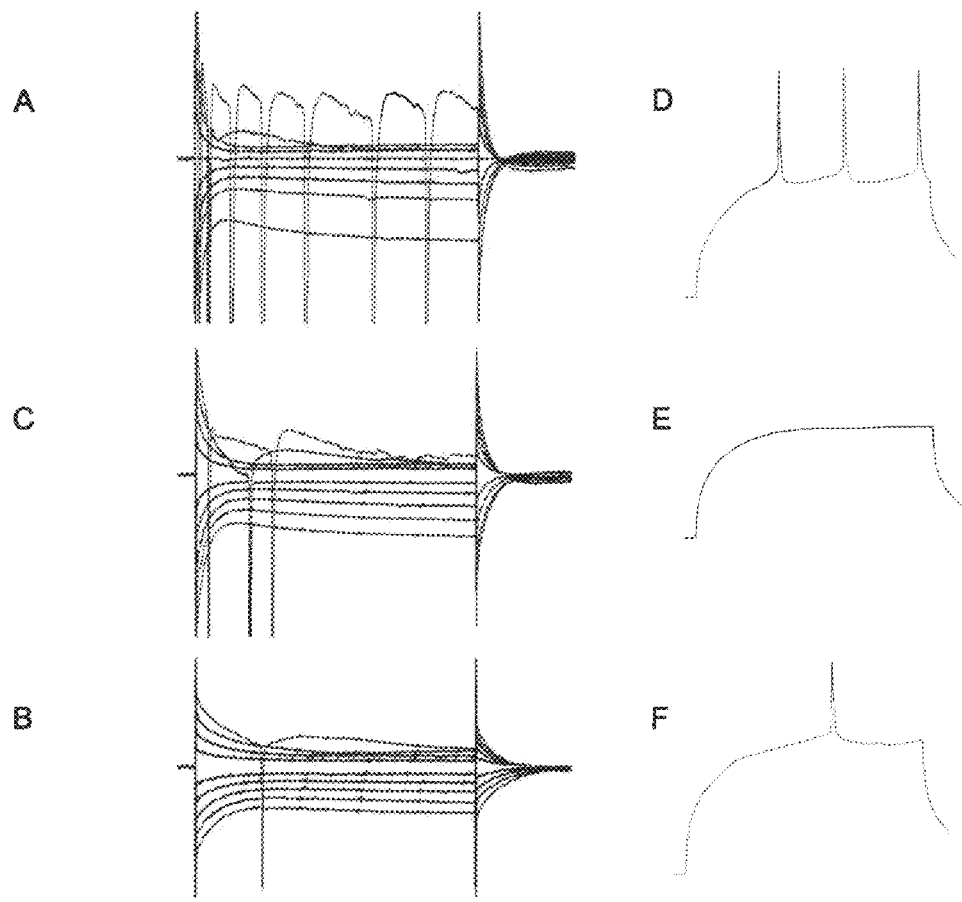
FIG. 2 depicts typical current voltage relationship in a cortical neuron (A=Control: B=Geraniol: C=After Washout) and the typical response of a cortical neuron following depolarizing current pulse (D=Control condition: E=in the presence of geraniol: F=After recovery).

Typical current-voltage (I-V) relation in a cortical neuron is shown in FIGS. 2A, 2B, and 2C. Superimposed responses to a series of 10 mV steps (250 ms) ranged from −110 to −20 mV are shown, (A) in control condition, (B) in presence of geraniol, and (C) after washout of the drug. Note the reduction in the membrane current amplitude and the inhibition of action potentials in presence of geraniol.

Typical response of a cortical neuron following a depolarizing current pulse of 0.4 nA is shown in FIGS. 2D, 2E and 2F, (D) in control condition, (E) in presence of geraniol, and (F) after recovery. Note the inhibition of action potential in presence of the tested compound.

Mean current-voltage plots for 6 cortical neurons are plotted in FIG. 1. Note the reduction of membrane currents in the presence of geraniol (test compound #4).

Figure 3:
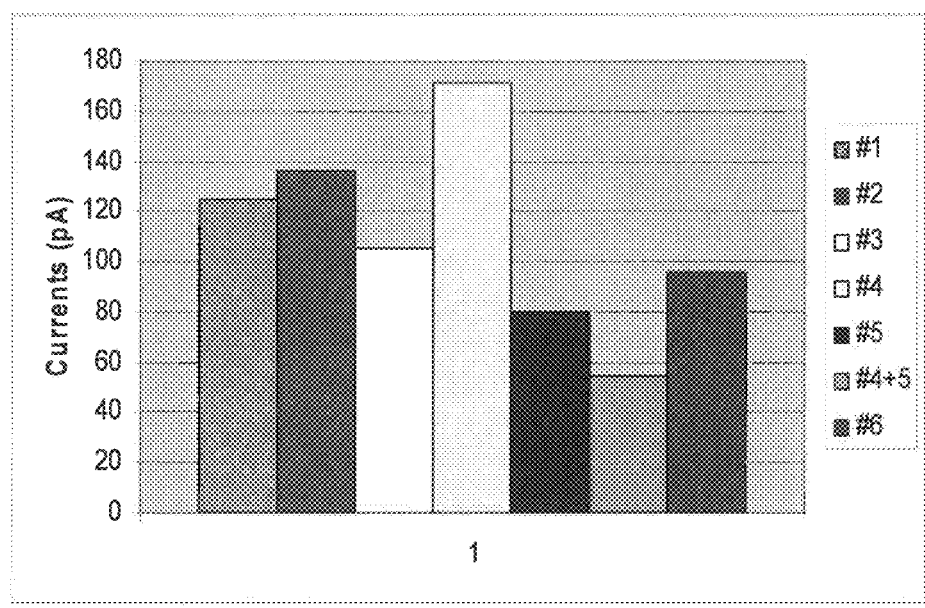
FIG. 3 graphically demonstrates the net current reduction in the presence of various treatments during patch clamp testing.

FIG. 3 shows the net current reduction in the presence of various naturally-derived geranium essential oils, and pure compounds, for each tested drug following the most negative voltage step (−110 mV). Samples 1, 2 and 6 are examples of naturally-derived geranium oils; sample 3 is the synthetic composition as set out in Table 1, sample 4 is pure geraniol, sample 5 is pure citronellol and sample 4+5 is 50:50 (by volume) combination of geraniol and citronellol. Net current represents the difference between current measured in control condition and in presence of tested compound, in response to the same voltage step. Note that of the compounds tested, sample #4 (geraniol) resulted in the greatest inhibition (current differential between control and tested compound).

Although the descriptions above contain specific examples of the compounds used at a given concentration, it is expected that the compounds are safe and effective when used at a range of concentrations and when mixed with one or more of the stated additional compounds in different ratios than described. Hence, use of any one of the stated additional compounds, or combinations thereof, in any concentration, will be determined to be effective and within the scope of the presently claimed and disclosed invention(s).

Although the examples above contain many specifics, these should not be construed as limiting the scope of the presently claimed and disclosed invention(s) but as merely providing illustrations of some of the presently preferred embodiments of the presently claimed and disclosed invention(s). Various other embodiments and ramifications are possible within its scope.

REFERENCES

1. Kalso, E Sodium Channel Blockers in Neuropathic Pain, Current Pharmaceutical Design, Volume 11, Number 23, September 2005, pp. 3005-3011(7).
2. Sindrup, Søren H.; Otto, Marit; Finnerup, Nanna B. Jensen, Troels S. Antidepressants in the Treatment of Neuropathic Pain Basic & Clinical Pharmacology & Toxicology, Volume 96, Number 6, June 2005, pp. 399-409(11).
3. Jensen T S. Anticonvulsants in neuropathic pain: rationale and clinical evidence. Eur J Pain. 2002; 6 Suppl A:61-8.
4. Kingery W S. A critical review of controlled clinical trials for peripheral neuropathic pain and complex regional pain syndromes. Pain 1997; 73:123-139.
5. Elon Eisenberg, MD; Ewan D. McNicol, RPh; Daniel B. Carr, MD Efficacy and Safety of Opioid Agonists in the Treatment of Neuropathic Pain of Nonmalignant Origin JAMA. 2005; 293:3043-3052.
6. Fromm G H. Baclofen as an adjuvant analgesic. J Pain Symptom Management 1994;9(8):500-509.
7. Eide K, Stubhaug A, Oye I, Breivik H. Continuous subcutaneous administration of the N-methyl-D-aspartic acid (NMDA) receptor antagonist ketamine in the treatment of postherpetic neuralgia. Pain 1995; 61(2):221-8.
8. Sindrup S H, Jensen T S. Efficacy of pharmacological treatments of neuropathic pain: an update and effect related to mechanism of drug action. Pain 1999; 83(3): 389-400.
9. Kronenberg R H. Ketamine as an analgesic: parenteral, oral, rectal, subcutaneous, transdermal and intranasal administration. J Pain Palliat Care Pharmacother. 2002; 16(3):27-35.
10. Greenway F L, Frome B M, Engels T M 3rd, McLellan A. Temporary relief of postherpetic neuralgia pain with topical geranium oil. Am J Med 2003 November; 115(7): 586-7.
11. Vendruscolo A, Takaki I, Bersani-Amado L E, Dantas J A, Bersani-Amado C A, Cuman R K. N Antiinflammatory and antinociceptive activities of zingiber officinale roscoe essential oil in experimental animal models. Ind J Pharm Vol 38 No 1 Pg 58-59 2006.
12. Nicoletta Galeotti, Lorenzo Di Cesare Mannelli, Gabriela Mazzanti, Alessandro Bartolini, Carla Ghelardini Menthol: a natural analgesic compound Neuroscience Letters 322 (2002) 145-148 NEUROLOGY 2005; 65:812-819.
13. David J. Rog, BMBS, Turo J. Nurmikko, PhD, Tim Friede, PhD and Carolyn A. Young, MD Randomized controlled trial of cannabis-based medicine in central pain in multiple sclerosis Neurology 2005; 65:812-819.
14. Alan D. Wickenden, K+ channels as therapeutic drug targets Pharmacology & Therapeutics 94 (2002) 157-182.
15. New Jersey Dept of Health Hazardous Substance Fact Sheet July 1999 #0052.
16. http://Toxnet.nlm.nih.gov CASRN: 555-10-2.
17. Johnston, G. A. R. GABA Receptor Channel Pharmacology. Current Pharmaceutical Design 2005, 11, 1867-1885.
18. Granger et al. (+) and (−)-borneol: efficacious positive modulators of GABA action. Biochemical Pharmacology 69 (2005) 1101-1111.

| U.S. PATENT DOCUMENTS | | |
|---|---|---|
| 4,311,617 | January 1982 | Ansari |
| 4,599,677 | July 1986 | Lawless |
| 4,923,685 | May 1990 | Wuelkhitz |
| 4,940,583 | July 1990 | Thompson |
| 5,260,313 | November 1993 | Frome |
| 2003/0224072 | December 2003 | Frome |

All publications, patents and patent applications mentioned in this Specification are indicative of the level of skill of those skilled in the art to which the presently claimed and disclosed invention(s) pertains and are herein incorporated by reference to the same extent as if each individual publication, patent, or patent applications was specifically and individually indicated to be incorporated by reference in its entirety.

The scope of the presently claimed and disclosed invention(s) should be determined by the appended claims and their legal equivalents, rather than by those presented in the in vitro or in vivo studies or by the examples given. The presently claimed and disclosed invention(s) being thus described, it will be obvious that the same may be varied in many ways. Such variations are not to be regarded as a departure from the spirit and scope of the presently claimed and disclosed invention(s), and all such modifications as would be obvious to one skilled in the art are intended to be included within the scope of the following claims.

The embodiments of the invention in which an exclusive property or privilege is claimed are defined as follows:

1. A method of treating neuropathic pain comprising the steps of administering a therapeutically effective amount of at least one purified and/or synthetic terpene compound to a mammalian subject and inhibiting nerve cell transmission, wherein the therapeutically effective amount inhibits nerve cell transmission and reduces neuropathic pain, wherein the terpene compound is selected from the group consisting of citronellol or a combination of citronellol and geraniol, and pharmaceutically acceptable salts and esters thereof, and wherein the mammalian subject is a human.

2. The method of claim 1, wherein the terpene compound is a combination of geraniol and citronellol.

3. The method of claim 1, wherein the terpene compound is citronellol.

4. The method of claim 1, wherein the compound is in a composition, the composition having a form selected from the group consisting of a suspension, pill, gel, oil, cream, patch, spray and aerosol, and optionally, comprises at least one or more pharmaceutically acceptable diluent or excipient.

5. The method of claim 4, wherein the composition is suitable for administration in a manner selected from the group consisting of oral administration, topical administration, intranasal delivery, transdermal administration, and combinations thereof.

6. The method of claim 1, wherein the cause of the neuropathic pain is selected from the group consisting of diabetic peripheral neuropathy, herpes zoster, post herpetic neuralgia, trigeminal neuralgia, complex regional pain syndrome, reflex sympathetic dystrophy, phantom limb syndrome, chronic disease, trauma, impingement, drug exposure, toxic chemical exposure, current infection, past infection, impaired organ function, vascular disease, metabolic disease, cancer, cancer treatment, autoimmune disease, fibromylagia, multiple sclerosis, HIV, causalgia, sciatica, carpal tunnel, and idiopathic pain.

* * * * *